US012558103B2

(12) United States Patent
Dai et al.

(10) Patent No.: US 12,558,103 B2
(45) Date of Patent: Feb. 24, 2026

(54) REPAIR ASSEMBLY AND REPAIR ASSEMBLY IMPLANTATION DEVICE

(71) Applicant: CREATIVE MEDTECH (SUZHOU) CO., LTD, Suzhou (CN)

(72) Inventors: Gaoxu Dai, Beijing (CN); Wuen Han, Beijing (CN); Fan Yang, Beijing (CN)

( * ) Notice: Subject to any disclaimer, the term of this patent is extended or adjusted under 35 U.S.C. 154(b) by 588 days.

(21) Appl. No.: 18/056,404

(22) Filed: Nov. 17, 2022

(65) Prior Publication Data

US 2023/0080977 A1    Mar. 16, 2023

Related U.S. Application Data

(63) Continuation     of     application     No. PCT/CN2020/122561, filed on Oct. 21, 2020.

(30) Foreign Application Priority Data

May 29, 2020    (CN) .......................... 202010482429.4

(51) Int. Cl.
*A61B 17/128*            (2006.01)
(52) U.S. Cl.
CPC ................................ *A61B 17/1285* (2013.01)
(58) Field of Classification Search
CPC ........ A61B 17/1285; A61B 2017/0488; A61B 17/068; A61B 2017/0647; A61B 17/0487; A61B 17/064; A61F 2/2454; A61F 2/2463; A61F 2/246; A61F 2/2466
See application file for complete search history.

(56) References Cited

U.S. PATENT DOCUMENTS

| | | | |
|---|---|---|---|
| 6,752,813 B2 | 6/2004 | Goldfarb et al. | |
| 10,376,266 B2 | 8/2019 | Herman et al. | |
| 2004/0138683 A1 | 7/2004 | Shelton et al. | |
| 2005/0177180 A1 | 8/2005 | Kaganov et al. | |
| 2007/0049942 A1* | 3/2007 | Hindrichs ............. | A61F 2/2451 |
| | | | 623/13.14 |
| 2007/0282375 A1 | 12/2007 | Hindrichs et al. | |
| 2011/0082538 A1 | 4/2011 | Dahlgren et al. | |
| 2018/0125657 A1 | 5/2018 | Dahlgren et al. | |

(Continued)

FOREIGN PATENT DOCUMENTS

| | | |
|---|---|---|
| CN | 1997318 A | 7/2007 |
| CN | 102686185 A | 9/2012 |

(Continued)

OTHER PUBLICATIONS

International Search Report issued in International Application No. PCT/CN2020/122561 dated Mar. 10, 2021 (6 pages).

(Continued)

*Primary Examiner* — Shaun L David
*Assistant Examiner* — Rachael L Geiger

(57)            ABSTRACT

A repair assembly and a repair assembly implantation device are provided. The repair assembly comprises a first implant, a second implant, and a wire clamping device; the first implant and the second implant each comprises a first fastener, a second fastener, a transverse tube and a locking wire; the first fastener and the second fastener are connected to the transverse tube by means of connecting wires, and the locking wire is connected to the transverse tube; the wire clamping device is configured to clamp the locking wire.

15 Claims, 6 Drawing Sheets

(56) References Cited

U.S. PATENT DOCUMENTS

| | | | |
|---|---|---|---|
| 2019/0083264 A1 | 3/2019 | Jarral et al. | |
| 2020/0214792 A1* | 7/2020 | Tsubouchi | A61B 90/20 |
| 2021/0298739 A1* | 9/2021 | Binmoeller | A61B 17/0487 |

FOREIGN PATENT DOCUMENTS

| | | | |
|---|---|---|---|
| CN | 104135973 | A | 11/2014 |
| CN | 107847320 | A | 3/2018 |
| CN | 111568605 | A | 8/2020 |
| CN | 212234802 | U | 12/2020 |

OTHER PUBLICATIONS

Chinese Office Action issued in Chinese Application No. 202010482429. 4, issued Jun. 22, 2024 (19 pages).
Chinese Office Action issued in Chinese Application No. 202010482429. 4, issued Dec. 19, 2024 (18 pages).
European Office Action issued in European Application No. 20938179. 7-1122, issued Aug. 22, 2023 (6 pages).
European Supplementary Search Report issued in European Application No. 20938179.7-1122, issued Aug. 10, 2023 (5 pages).

* cited by examiner

REPAIR ASSEMBLY AND REPAIR ASSEMBLY IMPLANTATION DEVICE

CROSS-REFERENCE TO RELATED APPLICATIONS

The present disclosure is a continuation of International Application No. PCT/CN2020/122561, which claims priority to Chinese Patent Application No. 202010482429.4, entitled "Repair Assembly and Repair Assembly Implantation Device," and filed with the Chinese Patent Office on May 29, 2020, the contents of which are incorporated herein by reference in their entireties.

TECHNICAL FIELD

The present disclosure relates to the technical field of medical devices, and in particular, to a repair assembly and a repair assembly implantation device.

BACKGROUND ART

In the field of medical technologies, the repair surgeries often need to be performed for diseased human organs, including the surgery of closing two functional parts separated due to lesions in the human organs.

For the existing transcatheter mitral regurgitation repair and other surgeries requiring to close two functional parts separated due to lesions in the human organs, in most cases, the closing effect is achieved by performing suturing around the two functional parts separated due to lesions in the human organs, or inputting a plurality of surgical fastener nails successively around the two functional parts separated due to lesions in the human organs and then connecting the plurality of surgical fastener nails with connecting wires. The structure and the implantation manner of the repair assembly used to be implanted into the human body are both relatively complex, and are not conducive to rapid surgery and rapid recovery of patients after the surgery.

SUMMARY

An embodiment of the present disclosure provides a repair assembly, including a first implant, a second implant, and a suture clamping device;

the first implant and the second implant each include a first fastener nail, a second fastener nail, a transverse tube, and a locking suture; an opposite end of a nail-in end of the first fastener nail is connected with an end of the transverse tube by a connecting wire, and an opposite end of a nail-in end of the second fastener nail is connected with the other end of the transverse tube by a connecting wire, and the locking suture is connected to the transverse tube; and the suture clamping device is configured to be capable of tightly clamping the locking suture of the first implant and the locking suture of the second implant, so as to fix a spacing between the transverse tube of the first implant and the transverse tube of the second implant.

An embodiment of the present disclosure provides a repair assembly implantation device, including an implant implantation mechanism and the repair assembly mentioned above, and the implant implantation mechanism is configured to implant the repair assembly into a human organ.

BRIEF DESCRIPTION OF DRAWINGS

In order to more clearly illustrate the technical solutions in embodiments of the present disclosure or in the prior art, drawings which need to be used in the descriptions of the embodiments or the prior art will be introduced briefly below, and apparently, the drawings in the descriptions below are for some embodiments of the present disclosure, and those ordinarily skilled in the art still could obtain other drawings according to these drawings without any creative effort.

Figure 1:
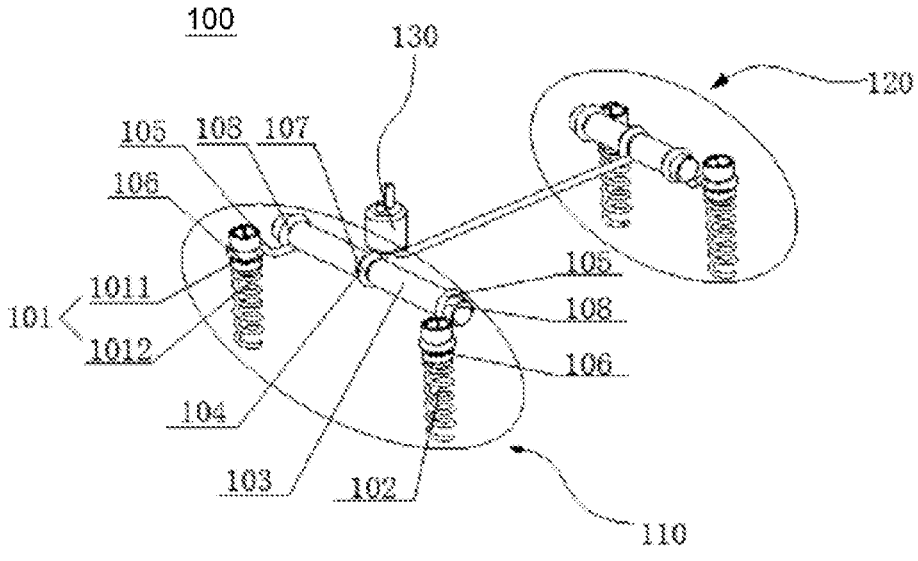
FIG. 1 is a schematic view of an overall structure of a repair assembly provided in an embodiment of the present disclosure.

Reference signs: 100—repair assembly; 110—first implant; 120—second implant; 101—first fastener nail; 1011—nail base; 1012—helical portion; 102—second fastener nail; 103—transverse tube; 104—locking suture; 105—connecting wire; 106—wiring slot; 107—suture locking slot; 108—wire winding slot; 130—suture clamping device; 210—support base; 221—bending-adjusting handle; 2210—bending-adjusting knob; 2211—bending-adjusting screw rod; 2212—adjusting block; 222—bending-adjusting sheath tube; 223—translation assembly; 2231—adjusting knob; 2232—adjusting gear; 2233—adjusting rack; 2234—limiting block; 2241—upper rotating shell; 2242—lower rotating shell; 2243—rotating buckle; 231—implantation handle; 2310—sealing base; 2311—housing; 2312—first branch handle; 2313—second branch handle; 201—main tube; 2011—limiting hole; 202—rotating portion; 2021—first rotating portion; 2022—second rotating portion; 2001—end connector; 2002—first connecting rod part; 2003—first rotating shell; 2004—helical spring; 2005—second connecting rod part; 2006—second rotating shell; 2314—third branch handle; 23141—end suture outlet bushing; 23142—third connecting rod part; 232—first delivery cable assembly; 2321—first delivery tube; 2322—first delivery cable; 2323—first pin; 230—tapered surface; 233—second delivery cable assembly; 300—unidirectional rotating structure; 310—ratchet; 320—pawl member; 301—avoidance hole; 400—anti-rotation protection element; 500—push structure; 510—push handle; 520—first gear; 530—second gear; 540—third gear; 600—compressing structure; 234—locking suture delivery tube; 235—equipartition tube; 241—operating handle; 2411—rotating barrel; 2412—knob; 242—suture-clamping-device delivery cable assembly.

DETAILED DESCRIPTION OF EMBODIMENTS

In order to make objectives, technical solutions, and advantages of the embodiments of the present disclosure clearer, the technical solutions in the embodiments of the present disclosure will be described clearly and completely below in conjunction with the drawings in the embodiments of the present disclosure, and apparently, some but not all embodiments of the present disclosure are described. Generally, components in the embodiments of the present disclosure described and shown in the drawings herein may be arranged and designed in different configurations.

Therefore, the detailed descriptions below of the embodiments of the present disclosure provided in the drawings are not intended to limit the scope of protection of the present disclosure, but merely represent chosen embodiments of the present disclosure. Based on the embodiments in the present disclosure, all of other embodiments, obtained by those ordinarily skilled in the art without any creative effort, shall fall within the scope of protection of the present disclosure.

It should be noted that similar reference signs and letters represent similar items in the following drawings, therefore, once a certain item is defined in one drawing, it is not needed to be further defined or explained in subsequent drawings.

In the descriptions of the present disclosure, it should be noted that the orientation or positional relationship indicated by the terms "front", "rear", "inner", "outer", etc. are based on the orientation or positional relationship shown in the drawings, or the orientation or positional relationship in which the inventive product is usually placed in use, and they are only for the convenience of describing the present disclosure and simplifying the descriptions, rather than indicating or implying that the related device or element must be in a specific orientation, or constructed or operated in a specific orientation, therefore they cannot be understood as limitations to the present disclosure. Besides, terms "first", "second", "third", etc. are merely used to distinguish the descriptions, but cannot be construed as indicating or implying importance in the relativity.

In the descriptions of the present disclosure, it should be further illustrated that, unless otherwise specifically regulated and defined, the terms "provide", "install", "link", and "connect" should be understood in a broad sense, for example, a connection may be a fixed connection, a detachable connection, or an integrated connection; it may be a mechanical connection or an electrical connection; it may be direct joining or indirect joining through an intermediary, and it also may be inner communication between two elements. For those ordinarily skilled in the art, specific meanings of the above-mentioned terms in the present disclosure could be understood according to specific circumstances.

The repair assembly and the repair assembly implantation device provided by the present disclosure alleviate the technical problems that the structure and the implantation manner of the repair assembly implanted into the human body are both relatively complex, and are not conducive to rapid surgery and rapid recovery of patients after the surgery.

Some embodiments of the present disclosure are described in detail below in combination with the drawings. The following embodiments and features in the embodiments may be combined with each other without conflict.

The present embodiment provides a repair assembly 100. Referring to FIG. 1, the repair assembly 100 includes a first implant 110, a second implant 120, and a suture clamping device 130. The first implant 110 and the second implant 120 each include a first fastener nail 101, a second fastener nail 102, a transverse tube 103, and a locking suture 104; an opposite end of a nail-in end of the first fastener nail 101 an end of the transverse tube 103 are connected by a connecting wire, an opposite end of a nail-in end of the second fastener nail 102 and the other end of the transverse tube 103 are connected by a connecting wire 105, and the locking suture 104 is connected to the transverse tube 103; the suture clamping device 130 is configured to be capable of tightly clamping the locking suture 104 of the first implant 110 and the locking suture 104 of the second implant 120, so as to lock a spacing between the transverse tube 103 of the first implant 110 and the transverse tube 103 of the second implant 120.

Figure 2:
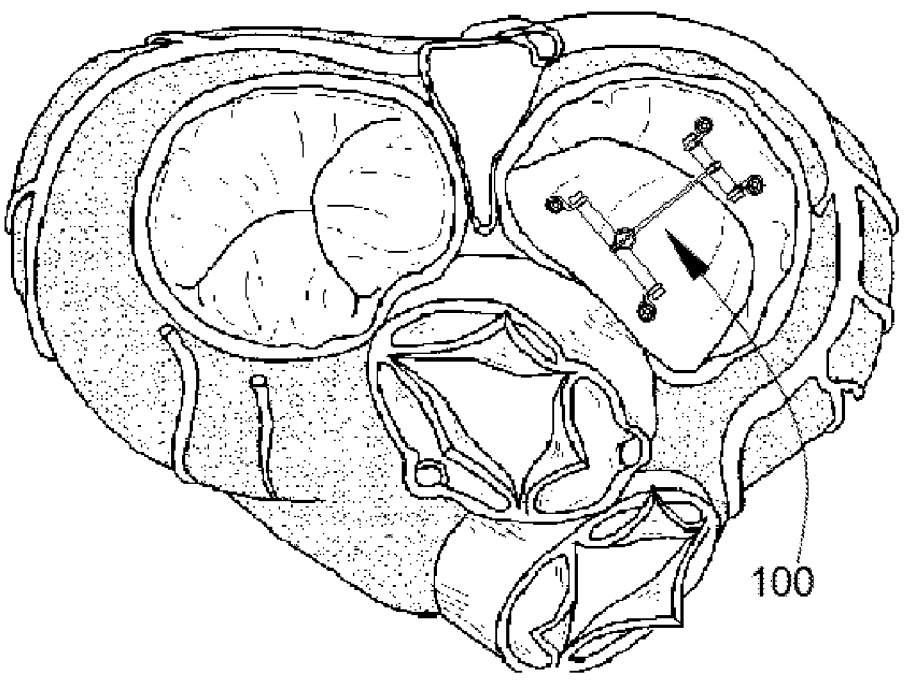
FIG. 2 is a schematic view of an application scenario of the repair assembly provided in an embodiment of the present disclosure.

The repair assembly 100 provided in the present embodiment can be applied to a surgery in which two functional parts separated due to lesions in the human organs need to be closed. During the surgery, by using a bending-adjusting sheath tube (bending-adjustable sheath tube) and an implantation mechanism cooperating with the bending-adjusting sheath tube, the first fastener nail 101 and the second fastener nail 102 of the first implant 110 can be delivered to one part of the two functional parts separated due to lesions in the human organs, and the first fastener nail 101 and the second fastener nail 102 of the second implant 120 are delivered to the other part of the two functional parts separated due to lesions in the human organs, then the suture clamping device 130 is delivered to between the transverse tube 103 of the first implant 110 and the transverse tube 103 of the second implant 120 by using the bending-adjusting sheath tube and a delivering mechanism cooperating with the bending-adjusting sheath tube, and the suture clamping device 130 is made to tightly clamp the locking suture 104 of the first implant 110 and the locking suture 104 of the second implant 120, so as to fix the spacing between the transverse tube 103 of the first implant 110 and the transverse tube 103 of the second implant 120; thus, the two functional parts separated due to lesions in the human organs can be closed with the repair assembly 100. A specific application scenario thereof may be as shown in FIG. 2, and the repair assembly is applied to the transcatheter mitral regurgitation repair or other surgeries in which two functional parts separated due to lesions in the human organs are required to be closed.

In the prior art, generally, a technical solution of closing (suturing) or surrounding two functional parts separated due to lesions in the human organs is as follows: inputting a plurality of surgical fastener nails in sequence, and then connecting the plurality of surgical fastener nails with each other by using the connecting wires, so as to achieve the closing effect. However, in the present embodiment, an overall structure of the repair assembly 100 provided in the present embodiment is relatively simple, and a repairing process can be realized just by inputting the first fastener nail 101, the second fastener nail 102, and one suture clamping device 130 in sequence. Compared with the prior art, the present embodiment can obviously shorten the time required for the surgery, and is conducive to rapidly complete the closing surgery. Moreover, as the operation time is short, and it is not likely to fail later, the repair assembly 100 provided in the present embodiment, after being implanted into the human organs, is also conducive to rapid recovery of patients after the surgery. In an optional example of the present embodiment, the first fastener nail 101 and the second fastener nail 102 may be of the same or different structures, as long as it is ensured that the first fastener nail 101 and the second fastener nail 102 can be implanted into the human organs.

In an optional example of the present embodiment, the first fastener nail 101 and the second fastener nail 102 may be formed in a helical shape respectively, in this way, the first fastener nail 101 and the second fastener nail 102 can be fixed in the human organs and tissues in a rotating manner. Specifically, referring to FIG. 1, in the present embodiment, the first fastener nail 101 and the second fastener nail 102 each include a nail base 1011 and a helical portion 1012, an end of the helical portion 1012 is the nail-in end, an opposite end of the nail-in end of the helical portion 1012 is connected to the nail base 1011, and the nail base 1011 is connected to the connecting wire 105. It can be understood that the nail base 1011 and the helical portion 1012 can move helically at the same time, facilitating fixing the helical portion 1012 in the human organs and tissues.

In addition, referring to FIG. 1, in the present embodiment, the nail base 1011 is provided thereon with a wiring slot 106 configured to allow the connecting wire 105 to be embedded therein. The connecting wire 105 can be wound in the wiring slot 106. The wiring slot 106 plays a role of limiting the connecting wire 105, so that the connecting wire 105 is not easily detached from the nail base 1011.

Correspondingly, in the present embodiment, outer tube walls of the two ends of the transverse tube 103 are each provided with a wire winding slot 108 configured to allow the connecting wire 105 to be embedded therein. The connecting wire 105 can be wound in the wire winding slot 108. The wire winding slot 108 plays a role of limiting the connecting wires 105, so that the connecting wire 105 is not easily detached from the transverse tube 103.

It should be noted that the wiring slot 106 and the wire winding slot 108 can facilitate the installation of the connecting wire 105 and the connection of the first fastener nail 101 and the second fastener nail 102 onto the transverse tube 103.

It should be noted that, in other optional embodiments, the two ends of the transverse tube 103 are each provided with a wire passing hole, and the connecting wire 105 is configured to pass through the wire passing holes, in this way, the connecting wire 105 can be fixedly connected onto the transverse tube 103. Such embodiment also can facilitate connecting the first fastener nail 101 and the second fastener nail 102 on the transverse tube 103.

Referring to FIG. 1, in the present embodiment, the outer tube wall of the transverse tube 103 is further provided with a suture locking slot 107 configured to wind the locking suture 104. The suture locking slot 107 facilitates the installation of the locking suture 104, and the locking suture 104 is not easily detached from the suture locking slot 107.

In an optional embodiment, the nail base is provided thereon with the wiring slot 106 for winding the connecting wire 105, and the outer tube wall of the transverse tube 103 is provided thereon with the suture locking slot 107 for winding the locking suture 104. In addition, the outer tube walls of the two ends of the transverse tube 103 are each provided with the wire winding slot 108, and the connecting wire 105 is connected to the transverse tube 103 in a manner of being wound in the corresponding wire winding slot 108. Alternatively, the two ends of the transverse tube 103 are each provided with the wire passing hole, and the connecting wire 105 is connected to the transverse tube 103 in a manner of being fixed after passing through the corresponding wire passing hole. The present embodiment further provides a repair assembly implantation device. This repair assembly implantation device includes an implant implantation mechanism and the foregoing repair assembly 100, and the implant implantation mechanism is configured to implant the foregoing repair assembly 100 into human organs. Specifically, referring to FIG. 3, in combination with FIG. 1 and FIG. 2, the repair assembly implantation device provided in the present embodiment includes a support base 210, the implant implantation mechanism includes an implantation handle 231, a first delivery cable assembly 232, and a second delivery cable assembly 233, wherein the implantation handle 231 is mounted on the support base 210, and a proximal end of the first delivery cable assembly 232 and a proximal end of the second delivery cable assembly 233 are both connected to the implantation handle 231. The repair assembly implantation device also has the beneficial effects of shortening the operation time and being conducive to rapid recovery of patients after the surgery.

In practical use, the implantation handle 231 drives the first delivery cable assembly 232, and the first delivery cable assembly 232 can release the first fastener nail 101, thus implanting the first fastener nail 101 into the human organs. Similarly, the implantation handle 231 drives the second delivery cable assembly 233, and the second delivery cable assembly 233 can release the second fastener nail 102, thus implanting the second fastener nail 102 into the human organs. It should be noted that, in the present embodiment, the foregoing "proximal end" and "distal end" take as reference the position of the repair assembly implantation device relative to an operator in normal operation. For example, in this repair assembly implant device, an end relatively close to the operator is a "proximal end", and an end relatively far away from the operator is a "distal end".

Specifically, in the present embodiment, in a first working condition, a distal end of the first delivery cable assembly 232 can be sleeved on the opposite end of the nail-in end of the first fastener nail 101, and the first delivery cable assembly 232 can rotate under a driving effect of the implantation handle 231, and meanwhile drive the first fastener nail 101 to rotate. In a second working condition, the first delivery cable assembly 232 can release the first fastener nail 101 under the driving effect of the implantation handle 231.

Similarly, in the first working condition, a distal end of the second delivery cable assembly 233 can be sleeved on the opposite end of the nail-in end of the second fastener nail 102, and the second delivery cable assembly 233 can rotate under the driving effect of the implantation handle 231, and meanwhile drive the second fastener nail 102 to rotate. In the second working condition, the second delivery cable assembly 233 can release the second fastener nail 102 under the driving effect of the implantation handle 231.

Referring to FIG. 3 to FIG. 5 and FIG. 8 and FIG. 9, in the present embodiment, the repair assembly implantation device further includes a bending-adjusting sheath tube mechanism, wherein the bending-adjusting sheath tube mechanism includes a bending-adjusting handle 221 and a bending-adjusting sheath tube 222, the bending-adjusting handle 221 is mounted on the support base 210, the bending-adjusting sheath tube 222 is connected to the bending-adjusting handle 221, and the first delivery cable assembly 232 and the second delivery cable assembly 233 both pass through the bending-adjusting sheath tube 222.

It should be noted that the bending-adjusting handle 221 can adjust a bending degree of the bending-adjusting sheath tube 222, and different bending degrees of the bending-adjusting sheath tube 222 are followed by different implantation positions and implantation angles of the first delivery cable assembly 232 and the second delivery cable assembly 233. That is to say, by changing the bending degree of the bending-adjusting sheath tube 222, the bending-adjusting handle 221 can change the implantation positions and the implantation angles of the first delivery cable assembly 232 and the second delivery cable assembly 233.

Specifically, in the present embodiment, the bending-adjusting handle 221 includes a bending-adjusting knob 2210, a bending-adjusting screw rod 2211, and an adjusting block 2212, the adjusting block 2212 is sleeved over the bending-adjusting screw rod 2211 in a threaded manner, a bending-adjusting wire is connected between a proximal end of the bending-adjusting sheath tube 222 and the adjusting block 2212, and a proximal end of the bending-adjusting screw rod 2211 is connected to the bending-adjusting knob 2210.

In this way, in practical operations, by rotating the bending-adjusting knob 2210, the bending-adjusting screw rod 2211 can rotate synchronously, the adjusting block 2212 slides along a length direction of the bending-adjusting screw rod 2211. In the sliding process of the adjusting block 2212, by tensioning or releasing the bending-adjusting wire, the bending-adjusting wire acts on the bending-adjusting sheath tube 222, so as to change the bending degree of the bending-adjusting sheath tube 222.

Figure 4:
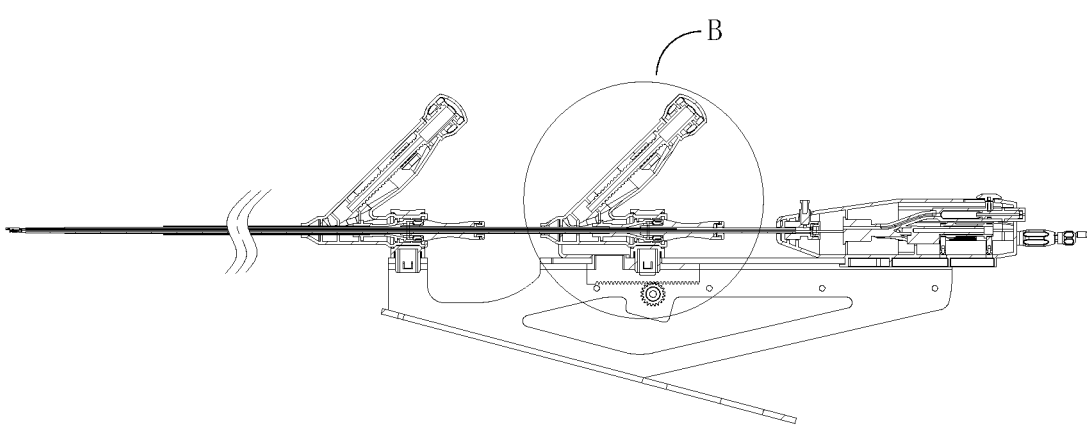
FIG. 4 is a front sectional view of FIG. 3.
Figure 8:
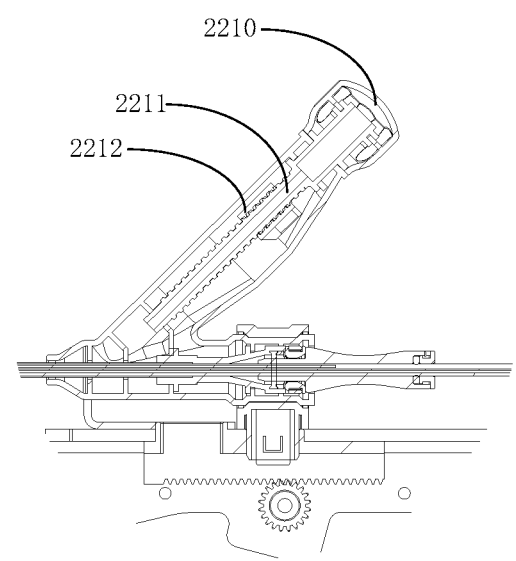
FIG. 8 is a partial structural enlarged view of a part B in FIG. 4.

In an optional embodiment, the bending-adjusting sheath tube mechanism includes a bending-adjusting handle 221 and the bending-adjusting sheath tube 222 connected to the bending-adjusting handle 221, and the bending-adjusting handle 221 is mounted on the support base 210, wherein a connection structure of the bending-adjusting handle 221 and the bending-adjusting sheath tube 222 is shown in FIG. 4 and FIG. 8 in detail. The bending-adjusting handle 221 includes a bending-adjusting knob 2210, a bending-adjusting screw rod 2211, and an adjusting block 2212, the adjusting block 2212 is sleeved over the bending-adjusting screw rod 2211 in a threaded manner, a bending-adjusting wire is connected between a distal end of the bending-adjusting sheath tube 222 and the adjusting block 2212, and the proximal end of the bending-adjusting screw rod 2211 is connected to the bending-adjusting knob 2210. By rotating the bending-adjusting knob 2210, the bending-adjusting screw rod 2211 can be rotated, further making the adjusting block 2212 slide along the length direction of the bending-adjusting screw rod 2211, to further tension or release the bending-adjusting wire, so as to achieve the function of adjusting the bending degree of the bending-adjusting sheath tube 222.

It should be noted that, in an optional embodiment, the number of foregoing bending-adjusting sheath tube mechanisms may be one, two, three, etc.

Figure 3:
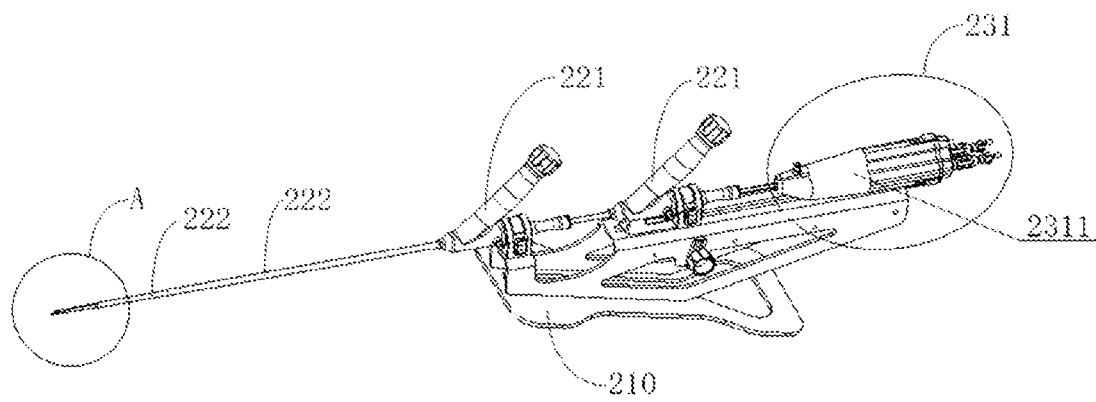
FIG. 3 is a schematic view of an overall structure of a repair assembly implantation device, mounted with the repair assembly, provided in an embodiment of the present disclosure, wherein connecting wires and locking sutures in the repair assembly are not shown.
Figure 9:
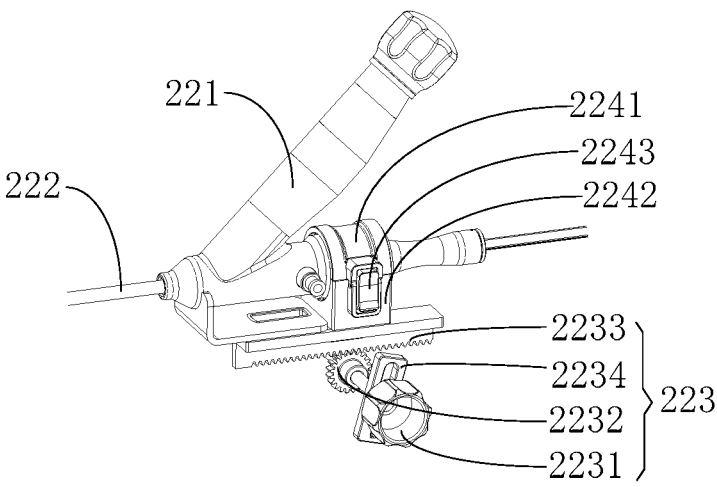
FIG. 9 is a schematic view of a connecting structure for connection between a bending-adjusting sheath tube mechanism and a support base, with the support base not shown.

In the present embodiment, the number of bending-adjusting sheath tube mechanisms is two. As shown in FIG. 3, FIG. 4, and FIG. 9, the two bending-adjusting sheath tube mechanisms are mounted on the proximal end and a distal end of the support base 210 respectively, and the bending-adjusting sheath tube 222 in the bending-adjusting sheath tube mechanism located at the proximal end passes through the bending-adjusting sheath tube 222 in the bending-adjusting sheath tube mechanism located at the distal end.

It should be noted that, in the present embodiment, the bending-adjusting sheath tube mechanism located at the distal end is fixedly connected to the support base 210, and the bending-adjusting sheath tube mechanism located at the proximal end is mounted on the support base 210 through a translation assembly 223.

In an optional embodiment, two bending-adjusting sheath tube mechanisms described in the above are mounted on the support base 210 at the front and rear, the bending-adjusting sheath tube 222 of the bending-adjusting sheath tube mechanism located at the rear passes through the bending-adjusting sheath tube 222 of the bending-adjusting sheath tube mechanism located at the front, the bending-adjusting sheath tube mechanism located at the front is fixed on the support base 210, and the bending-adjusting sheath tube mechanism located at the rear is mounted on the support base 210 through the translation assembly 223.

Specifically, referring to FIG. 9, in the present embodiment, the translation assembly 223 includes an adjusting rack 2233, a limiting block 2234, an adjusting knob 2231, and an adjusting gear 2232, wherein the adjusting rack 2233 is mounted on a bracket of the bending-adjusting sheath tube mechanism at the proximal end, the limiting block 2234 is connected to the support base 210, the limiting block 2234 is provided with a limiting long hole, one end of the adjusting knob 2231 is fixedly connected to a rotating shaft slidably fitted to (cooperating with) the foregoing limiting long hole, the adjusting gear 2232 is fixedly connected to an end of the rotating shaft away from the adjusting knob 2231, and the adjusting gear 2232 can be meshed with the adjusting rack 2233.

In practical use, by rotating the adjusting knob 2231, the bracket of the bending-adjusting sheath tube mechanism located at the proximal end can move relative to the support base 210. The rotating shaft can slide to limiting positions of the limiting long hole at two ends thereof. At one limiting position thereof, the adjusting gear 2232 can be detached from the adjusting rack 2233, and the bending-adjusting sheath tube mechanism located at the proximal end can be taken down. At this point, the operator can primarily adjust the implantation positions and the implantation angles of the first delivery cable assembly 232 and the second delivery cable assembly 233 by using the bending-adjusting sheath tube mechanism at the distal end. Then, the implantation positions and the implantation angles of the first delivery cable assembly 232 and the second delivery cable assembly 233 can be adjusted for a second time by using the bending-adjusting sheath tube mechanism located at the proximal end, thus improving the implantation accuracy.

In an optional embodiment, the adjusting rack 2233 is provided at the bottom of the bracket of the bending-adjusting sheath tube mechanism located at the rear, one end of the adjusting knob 2231 is fixedly connected to the rotating shaft, the rotating shaft passes through the limiting long hole on the limiting block 2234, the adjusting gear 2232 is fixed to an end of the rotating shaft away from the adjusting knob 2231, the limiting block 2234 is fixed to the support base 210, and the rotating shaft can slide along the limiting long hole and is located at the two limiting positions of the limiting long hole. At one limiting position thereof, the adjusting gear 2232 can be meshed with the adjusting rack 2233, the adjusting rack 2233 extends along a front-rear direction, and by rotating the adjusting knob 2231, the bracket of the bending-adjusting sheath tube mechanism located at the rear can move back and forth relative to the support base 210. At the other limiting position, the adjusting gear 2232 can be detached from the adjusting rack 2233, at this point, the bending-adjusting sheath tube mechanism located at the rear can be taken down relative to the support base 210. With the above structure, the implantation positions and the implantation angles can be primarily adjusted by using the bending-adjusting sheath tube mechanism located at the front, and then the implantation positions and the implantation angles can be finely adjusted by using the bending-adjusting sheath tube mechanism located at the rear, thus improving the accuracy of the implantation positions.

In addition, in the present embodiment, the bending-adjusting handles 221 of the two bending-adjusting sheath tube mechanisms can be respectively rotatably connected to the brackets of the two bending-adjusting sheath tube mechanisms through different rotating structures.

Specifically, referring to FIG. 9, in the present embodiment, the rotating structure includes an upper rotating shell 2241, a lower rotating shell 2242, and a rotating buckle 2243, wherein the lower rotating shell 2242 is fixed to the support base 210, and the upper rotating shell 2241 and the lower rotating shell 2242 are connected with each other by the rotating buckle 2243.

In practical use, by opening the rotating buckle 2243, the bending-adjusting handle 221 can be clamped between the upper rotating shell 2241 and the lower rotating shell 2242. Alternatively, by opening the rotation buckle 2243, the bending-adjusting handle 221 also can be taken out from between the upper rotating shell 2241 and the lower rotating shell 2242.

It should be noted that, in the present embodiment, the bending-adjusting handle 221 is rotatably provided between the upper rotating shell 2241 and the lower rotating shell 2242, in this way, the implantation angle can be adjusted more conveniently.

In an optional embodiment, as shown in FIG. 9, the bending-adjusting handle 221 of the bending-adjusting sheath tube mechanism located at the front and the bending-adjusting handle 221 of the bending-adjusting sheath tube mechanism located at the rear both can be rotatably mounted on respective brackets through rotating structures. Specifically, this rotating structure may include an upper rotating shell 2241, a lower rotating shell 2242, and a rotating buckle 2243, the lower rotating shell 2242 is fixed to the support base 210, and the upper rotating shell 2241 and the lower rotating shell 2242 are connected with each other by the rotating buckle 2243. By opening the rotating buckle 2243, the bending-adjusting handle 221 of the bending-adjusting sheath tube mechanism can be clamped between the upper rotating shell 2241 and the lower rotating shell 2242, or the bending-adjusting handle 221 can be taken out from between the upper rotating shell 2241 and the lower rotating shell 2242. In addition, the bending-adjusting handle 221 of the bending-adjusting sheath tube mechanism can rotate between the upper rotating shell 2241 and the lower rotating shell 2242, thus the implantation angle can be adjusted more conveniently.

In an optional embodiment, the implant implantation mechanism includes an implantation handle 231, a first delivery cable assembly 232, and a second delivery cable assembly 233, wherein the implantation handle 231 is mounted on the support base 210, the first delivery cable assembly 232 and the second delivery cable assembly 233 both pass through the bending-adjusting sheath tube 222, and a proximal end of the first delivery cable assembly 232 and a proximal end of the second delivery cable assembly 233 are both connected to the implantation handle 231. The first delivery cable assembly 232 is configured in such a manner that, in the first working condition, the distal end of the first delivery cable assembly 232 can be sleeved on the opposite end of the nail-in end of the first fastener nail 101, and the first delivery cable assembly 232 can rotate under the driving effect of the implantation handle 231 so as to drive the first fastener nail 101 to rotate, and in the second working condition, the first delivery cable assembly 232 can release the first fastener nail 101 under the driving effect of the implantation handle 231. The second delivery cable assembly 233 is configured in such a manner that in the first working condition, the distal end of the second delivery cable assembly 233 can be sleeved on the opposite end of the nail-in end of the second fastener nail 102, and the second delivery cable assembly 233 can rotate under the driving effect of the implantation handle 231 so as to drive the second fastener nail 102 to rotate, and in the second working condition, the second delivery cable assembly 233 can release the second fastener nail 102 under the driving effect of the implantation handle 231. Referring to FIG. 3, FIG. 10, FIG. 11, FIG. 12, and FIG. 13, in the present embodiment, the above implantation handle 231 includes a housing 2311, a first branch handle 2312, and a second branch handle 2313, and the housing 2311 is mounted to the support base 210; the first branch handle 2312 and the second branch handle 2313 each include a main tube 201 and a rotating portion 202, the main tube 201 is inserted inside the housing 2311, the distal end of the rotating portion 202 is rotatably inserted into and connected to the inside of a proximal end of the main tube 201, and a proximal end of the rotating portion 202 is located outside the housing.

In the present embodiment, the distal end of the rotating portion 202 in the first branch handle 2312 is connected to the proximal end of the first delivery cable assembly 232, and the distal end of the rotating portion 202 in the second branch handle 2313 is connected to the proximal end of the second delivery cable assembly 233.

In this way, by rotating the rotating portion 202 in the first branch handle 2312, the first delivery cable assembly 232 rotates, and meanwhile drives the first fastener nail 101 to rotate. By rotating the rotating portion 202 in the second branch handle 2313, the second delivery cable assembly 233 rotates, and meanwhile drives the second fastener nail 102 to rotate.

Figure 5:
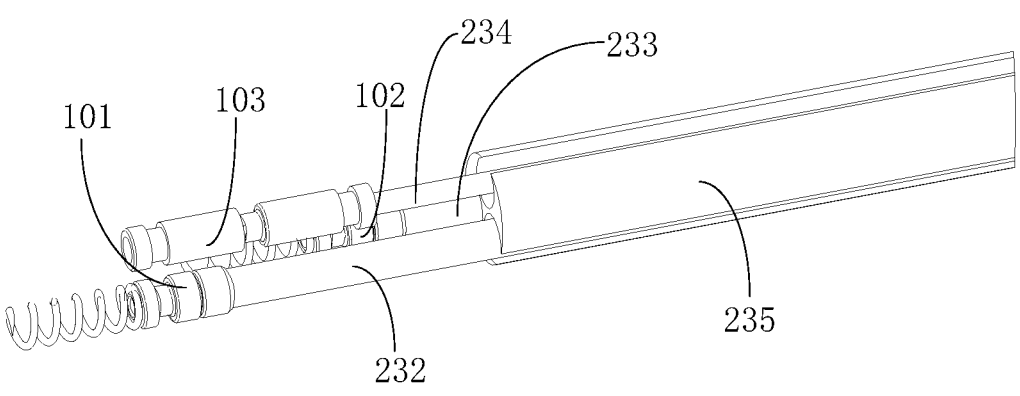
FIG. 5 is a partial structural enlarged view of a part A in FIG. 3.
Figure 6:
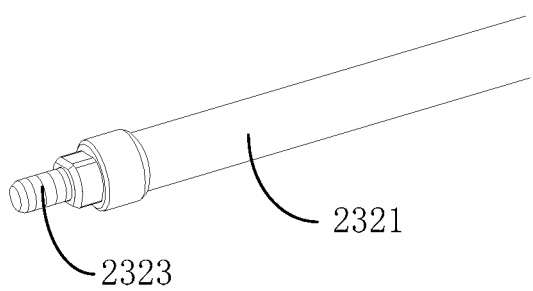
FIG. 6 is a structural schematic view of a distal end of a first delivery cable assembly in FIG. 5.
Figure 7:
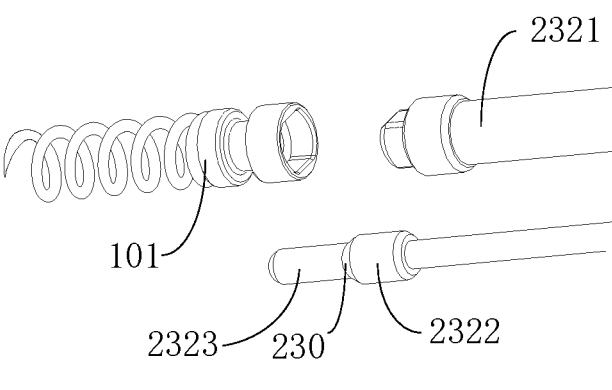
FIG. 7 is an exploded schematic view of a connecting structure of a first fastener nail and the distal end of the first delivery cable assembly in FIG. 5.

In an optional embodiment, the rotating portion 202 is rotatably connected to the main tube 201 in a manner that the distal end of the rotating portion is inserted inside the proximal end of the main tube 201, the proximal end of the rotating portion 202 is located outside the housing 2311, and in the first branch handle 2312: the distal end of the rotating portion 202 is connected to the proximal end of the first delivery cable assembly 232, and in the second branch handle 2313: the distal end of the rotating portion 202 is connected to the proximal end of the second delivery cable assembly 233. Referring to FIG. 5, FIG. 6, and FIG. 7, in the present embodiment, the first delivery cable assembly 232 includes a first delivery tube 2321, a first delivery cable 2322, and a first pin 2323, a distal end of the first delivery tube 2321 is sleeved on the opposite end of the nail-in end of the first fastener nail 101, and the first delivery tube 2321 is configured to drive the first fastener nail 101 to rotate synchronously, the first delivery cable 2322 passes through the first delivery tube 2321, a proximal end of the first pin 2323 is fixedly connected to a distal end of the first delivery cable 2322, and a distal end of the first pin 2323 is in threaded connection to the opposite end of the nail-in end of the first fastener nail 101, so that the first fastener nail 101 and the first delivery tube 2321 rotate synchronously.

In an optional embodiment, as shown in FIG. 7, the proximal end of the first pin 2323 abuts against the distal end of the first delivery cable 2322 through a tapered surface 230, the diameter of the tapered surface 230 gradually increases in a direction from the first pin 2323 to the first delivery cable 2322. An inner wall surface of the distal end of the first delivery tube 2321 is provided thereon with another tapered abutment surface matched with (cooperates with) the tapered surface 230, and the first delivery cable 2322 can drive the first pin 2323 to slide back and forth inside the first delivery tube 2321. Moreover, in cases where the tapered surface 230 abuts against the another tapered abutment surface on the inner wall surface of the distal end of the first delivery tube 2321, the first pin 2323 protrudes to a distal-most position relative to the first delivery tube 2321, at this point, the distal end of the first pin 2323 protrudes from the distal end of the first delivery tube 2321. The distal end of the first delivery tube 2321 is formed as a polygonal positioning portion, the opposite end of the nail-in end of the first fastener nail 101 is provided with a polygonal snap-fit groove snap-fitted with the polygonal positioning portion, and after the polygonal positioning portion is snap-fitted with the polygonal snap-fit groove, the first fastener nail 101 and the first delivery tube 2321 can rotate synchronously. In addition, an inner wall of the polygonal snap-fit groove is provided with an internal thread configured to be in threaded connection with the first pin 2323.

Similarly, in the present embodiment, the second delivery cable assembly 233 includes a second delivery tube, a second delivery cable, and a second pin, a distal end of the second delivery tube is sleeved on the opposite end of the nail-in end of the second fastener nail 102, the second delivery tube is configured to drive the second fastener nail 102 to rotate synchronously, the second delivery cable passes through the second delivery tube, a distal end of the second pin can be in threaded connection to a distal end of the second delivery cable, and the distal end of the second pin can be in threaded connection to the opposite end of the nail-in end of the second fastener nail 102, so that the second fastener nail and the second delivery tube rotate synchronously.

In an optional embodiment, the second delivery cable assembly 233 includes corresponding second delivery tube, second delivery cable, and second pin, a proximal end of the second pin is fixedly connected to the distal end of the second delivery cable, and the second pin is configured in such a manner that the distal end of the second pin can be in threaded connection to the opposite end of the nail-in end of the second fastener nail 102, the second delivery cable passes through the second delivery tube, and the second delivery tube is configured in such a manner that the distal end of the second delivery tube can be sleeved on the opposite end of the nail-in end of the second fastener nail

102, and enables the second fastener nail 102 to rotate synchronously with the second delivery tube.

As shown in FIG. 11 to FIG. 14, the rotating portion 202 includes a first rotating portion 2021 and a second rotating portion 2022, a distal end of the first rotating portion 2021 is rotatably sleeved on the proximal end of the main tube 201, a distal end of the second rotating portion 2022 is rotatably sleeved on the first rotating portion 2021, and the second rotating portion 2022 and a proximal end of the first rotating portion 2021 are both located outside the housing 2311.

In the first branch handle 2312, the distal end of the first rotating portion 2021 is connected to the proximal end of the first delivery tube 2321, and the distal end of the second rotating portion 2022 is connected to the proximal end of the first delivery cable 2322. In the second branch handle 2313, the distal end of the first rotating portion 2021 is connected to the proximal end of the second delivery tube, and the distal end of the second rotating portion 2022 is connected to the proximal end of the second delivery cable.

In the present embodiment, the first branch handle 2312 and the second branch handle 2313 each include a helical spring 2004.

In the first branch handle 2312, the distal end of the second rotating portion 2022 is connected to the proximal end of the first delivery cable 2322 by the helical spring 2004. In the second branch handle 2313, the distal end of the second rotating portion 2022 is connected to the proximal end of the second delivery cable by the helical spring 2004.

In an optional embodiment, the first rotating portion 2021 is rotatably connected to the main tube 201 in such a manner that the distal end of the first rotating portion 2021 is inserted inside the proximal end of the main tube 201, the first rotating portion 2021 has a through hole running through the first rotating portion 2021 in a front-back direction, the second rotating portion 2022 is rotatably connected to the first rotating portion 2021 in such a manner that the distal end of the second rotating portion 2022 is inserted inside the proximal end of the first rotating portion 2021, the proximal end of the first rotating portion 2021 and the second rotating portion 2022 are both located outside the housing 2311, and in the first branch handle 2312: the distal end of the first rotating portion 2021 is connected to the proximal end of the first delivery tube 2321, the distal end of the second rotating portion 2022 is connected to the proximal end of the first delivery cable 2322 through the helical spring 2004; and in the second branch handle 2313, the distal end of the first rotating portion 2021 is connected to the proximal end of the second delivery tube, and the distal end of the second rotating portion 2022 is connected to the proximal end of the second delivery cable through the helical spring 2004.

In the present embodiment, the working principle of implanting the first fastener nail 101 with the first branch handle 2312 is similar to the working principle of implanting the second fastener nail 102 with the second branch handle 2313. Below, the working principle of the first branch handle 2312 is described as follows by taking the implantation of the first fastener nail 101 with the first branch handle 2312 as an example.

When the first fastener nail 101 is implanted with the first branch handle 2312, the opposite end of the nail-in end of the first fastener nail 101 is in threaded connection to the distal end of the first pin 2323, and the opposite end of the nail-in end of the first fastener nail 101 is made to be sleeved on the distal end of the first delivery tube 2321, at this point, the tapered abutment surface on the inner wall surface of the distal end of the first delivery tube 2321 abuts against the tapered surface 230, the helical spring 2004 is in a stretched state, and an end surface of the opposite end of the nail-in end of the first fastener nail 101 abuts against a distal end surface of the first delivery tube 2321.

Then, by rotating the first rotating portion 2021, the first delivery tube 2321 rotates with the rotation of the first rotating portion 2021, and the first delivery tube 2321 drives the first fastener nail 101 to rotate forward, so that the nail-in end of the first fastener nail 101 is nailed into the human organs and tissues.

After being rotated in place, the second rotating portion 2022 is reversely rotated, then the first pin 2323 can be made to rotate relative to the first fastener nail 101, inside the first delivery tube 2321, so that the first pin 2323 is detached from the first fastener nail 101, at this point, under the effect of the resilience of the helical spring 2004, the first pin 2323 retracts back to the inside of the first delivery tube 2321.

It should be noted that, in the present embodiment, the helical spring 2004 can prevent, after the first pin 2323 is detached from the first fastener nail 101, the distal end of the first pin 2323 from damaging the human organs and tissues. Meanwhile, the helical spring 2004 also may ensure that, before the first pin 2323 is detached from the first fastener nail 101, the first pin 2323 always has a tendency to pull the first fastener nail 101 backwards, so that the end surface of the opposite end of the nail-in end of the first fastener nail 101 has a movement tendency to abut against the distal end surface of the first delivery tube 2321. In this way, it can be ensured that when the first pin 2323 is detached from the first fastener nail 101, the first delivery tube 2321 and the first fastener nail 101 are in a state of one being sleeved over the other, ensuring that the first fastener nail 101 does not rotate during the first pin 2323 reversely rotating relative to the first fastener nail 101, further ensuring that the first pin 2323 can be successfully detached from the first fastener nail 101.

Figure 13:
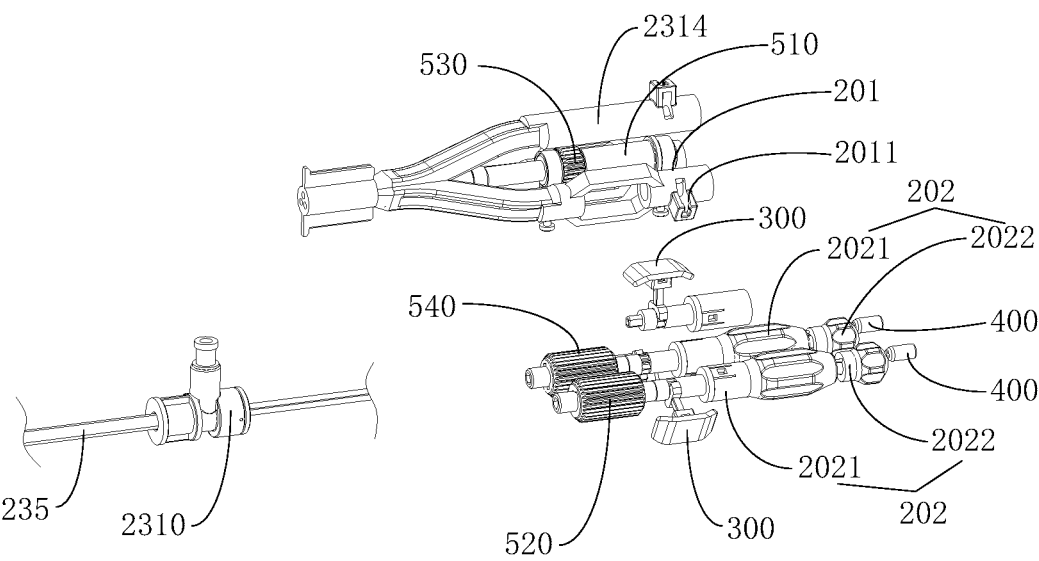
FIG. 13 is an exploded structural schematic view of the implantation handle shown in FIG. 10 in the housing-free state.
Figure 14:
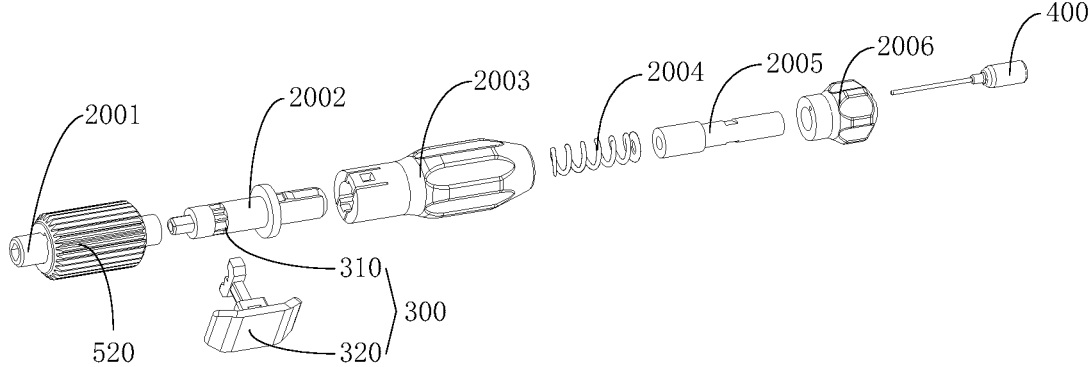
FIG. 14 is an exploded view of a partial structure of a first branch handle or a second branch handle in FIG. 13.

Referring to FIG. 13 and FIG. 14, the first branch handle 2312 and the second branch handle 2313 in the above each further include a unidirectional rotating structure 300, and in the first branch handle 2312 and/or the second branch handle 2313, the unidirectional rotating structure 300 is located between the first rotating portion 2021 and the main tube 201, and the unidirectional rotating structure 300 is configured to enable the first rotating portion 2021 to unidirectionally rotate only with respect to the main tube 201.

Specifically, as shown in FIG. 13 and FIG. 14, the first rotating portion 2021 includes an end connector 2001, a first connecting rod part 2002, and a first rotating shell 2003 which are connected in sequence, the end connector 2001 and the first connecting rod part 2002 are inserted inside the main tube 201, the unidirectional rotating structure 300 includes a pawl member 320 and a ratchet 310 provided on an outer circumferential surface of the first connecting rod part 2002, and the pawl of the pawl member 320 and the ratchet 310 are meshed with each other. In combination with FIG. 10, in the present embodiment, a limiting hole 2011 is provided on a tube wall of the main tube 201, and an end of the pawl member 320 away from the ratchet 310 passes through the limiting hole 2011.

In the present embodiment, the second rotating portion 2022 includes a second connecting rod part 2005 and a second rotating shell 2006, the second connecting rod part 2005 is inserted inside the first rotating shell 2003, the second rotating shell 2006 is connected to a proximal end of the second connecting rod part 2005, and a proximal end of the helical spring 2004 is connected to a distal end of the second connecting rod part 2005.

The working principle of the first branch handle 2312 is described still by taking the implantation of the first fastener nail 101 with the first branch handle 2312 as an example. In the present embodiment, the unidirectional rotating structure 300 can make the first delivery tube 2321 only rotate forwards along with the second rotating shell 2006. Specifically, in the process of operating the second rotating shell 2006 to rotate so as to make the first pin 2323 reversely rotate relative to the first fastener nail 101, the unidirectional rotating structure 300 can ensure that the first delivery tube 2321 does not rotate reversely along with the second rotating shell 2006, further ensuring that the first pin 2323 can be smoothly detached from the first fastener nail 101.

It should be noted that, the foregoing "rotate forwards (forward rotation)" and "rotate reversely (reverse rotation)" are relative concepts. If a relative positional relationship between the operator and the repair assembly implantation device is taken as a reference, if the "rotate forwards" is "rotate clockwise", the "rotate reversely" is "rotate counterclockwise". If the "rotate forwards" is "rotate counterclockwise", the "rotate reversely" is "rotate clockwise".

Besides, referring to FIG. 13 and FIG. 14, in the present embodiment, the first branch handle 2312 and the second branch handle 2313 each further include an anti-rotation protection element 400, and in the first branch handle 2312 and/or the second branch handle 2313: the anti-rotation protection element 400 can be detachably connected to the first rotating portion 2021 and the second rotating portion 2022 simultaneously, and the anti-rotation protection element 400 is configured to make the first rotating portion 2021 and the second rotating portion 2022 synchronously rotate.

Specifically, as shown in FIG. 14, the proximal end surface of the first rotating portion 2021 is provided with a first positioning hole, the second rotating portion 2022 is provided with a second positioning hole running in the front-back direction, and one end of the anti-rotation protection element 400 extends into the first positioning hole after passing through the second positioning hole.

In this way, the second rotating portion 2022 can be prevented from rotating relative to the first rotating portion 2021 when the first rotating portion 2021 is rotated. In addition, when the second rotating portion 2022 needs to be rotated alone, it just needs to pull out the anti-rotation protection element 400.

In addition, referring to FIG. 10 to FIG. 13, in the present embodiment, the main tube 201 of the first branch handle 2312 and the main tube 201 of the second branch handle 2313 are connected to each other to form a main frame, and the main frame is slidably inserted inside the housing 2311.

In the present embodiment, the housing 2311 of the implantation handle 231 is provided thereon with an avoidance hole 301 for allowing the pawl member 320 to extend out therefrom. With continued reference to FIG. 10 to FIG. 13, the implantation handle 231 further includes a push structure 500, wherein the push structure 500 includes a push handle 510, a first gear 520, a second gear 530, and a third gear 540, the push handle 510 is connected to the main frame, the first gear 520, the second gear 530, and the third gear 540 are meshed in turn, moreover, the first gear 520 is connected to the first rotating portion 2021 of the first branch handle 2312, the second gear 530 is connected to the push handle 510, and the third gear 540 is connected to the first rotating portion 2021 of the second branch handle 2313.

In an optional embodiment, the push handle 510 and the first gear 520, the second gear 530, and the third gear 540 that are meshed in turn; the push handle 510 is connected to the foregoing main frame, the second gear 530 is connected to the push handle 510, the first gear 520 is connected to the outside of the end connector 2001 of the first rotating portion 2021 of the first branch handle 2312, and the third gear 540 is connected to the outside of the end connector 2001 of the first rotating portion 2021 of the second branch handle 2313. Specifically, a tube wall of the main tube 201 of the first branch handle 2312 is provided with a window for allowing the first gear 520 to be exposed, and a tube wall of the main tube 201 of the second branch handle 2313 is provided with a window for allowing the third gear 540 to be exposed.

In the present embodiment, in the process of implanting the fastener nails into the human organs and tissues with the first branch handle 2312 and the second branch handle 2313, the push structure 500 can push the main frame to slide forwards relative to the housing 2311, so as to avoid the main frame from applying a backward pulling force to the first fastener nail 101 and the second fastener nail 102, thus ensuring that the first fastener nail 101 and the second fastener nail 102 can be quickly screwed into the human organs and tissues.

A thread pitch of the thread on the first pin 2323 is equal to a tooth pitch of the second gear 530 on the push handle 510, in this way, a distance by which the main frame slides forward relative to the housing 2311 is equal to a distance by which the first fastener nail 101 is nailed into the human organs and tissues.

In addition, in the present embodiment, the first gear 520, the second gear 530, and the third gear 540 are meshed in turn, in this way, in cases where the first rotating portion 2021 of the first branch handle 2312 is rotated, the first rotating portion 2021 of the second branch handle 2313 can rotate therewith, thus realizing the function of implanting the first fastener nail 101 and the second fastener nail 102 simultaneously, and effectively improving the implantation efficiency. That is to say, when the first rotating portion 2021 of the first branch handle 2312 or the first rotating portion 2021 of the second branch handle 2313 is rotated, the first rotating portion 2021 of the other one of the first branch handle 2312 and the second branch handle 2313 is also rotated therewith, and further the first fastener nail 101 and the second fastener nail 102 are implanted simultaneously, improving the implantation efficiency.

Meanwhile, in the present embodiment, by meshing the first gear 520, the second gear 530, and the third gear 540 in turn, it also can ensure that no matter which fastener nail is implanted, the main frame can slide forwards relative to the housing 2311.

In addition, in the present embodiment, the implantation handle 231 further includes a third branch handle 2314, a distal end of the third branch handle 2314 is connected to an inner wall of the housing 2311, and the third branch handle 2314 is provided with a suture passing cavity running therethrough. The implant implantation mechanism further includes a locking suture delivery tube 234, wherein the locking suture delivery tube 234 passes through the bending-adjusting sheath tube 222, a proximal end of the locking suture delivery tube 234 is connected to the distal end of the third branch handle 2314, and the locking suture 104 passes through the locking suture delivery tube 234 and the suture passing cavity simultaneously.

In this way, after the first implant 110 is implanted, the locking suture 104 in the first implant 110 can be conveniently led out, facilitating the locking and suturing with the locking suture 104 in the second implant 120 later. Alternatively, after the second implant 120 is implanted, the locking suture 104 in the second implant 120 can be conveniently led out, facilitating the locking and suturing with the locking suture 104 in the first implant 110 later.

Figure 15:
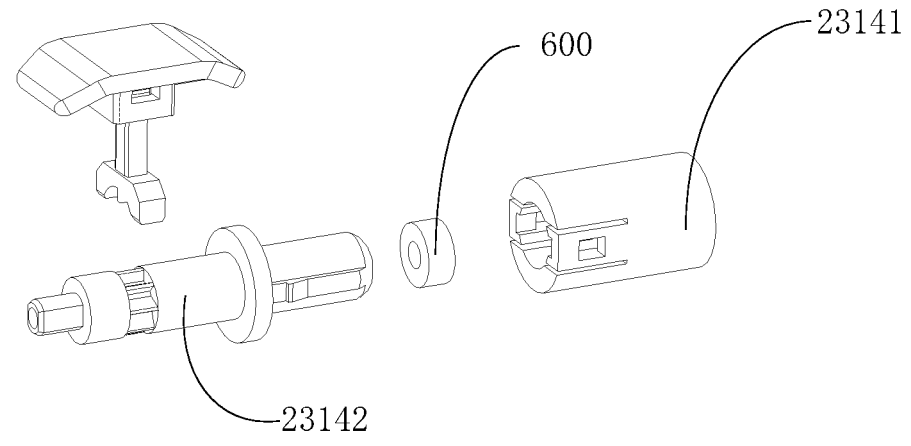
FIG. 15 is an exploded view of a partial structure of a third branch handle in FIG. 13.

In an optional embodiment, the distal end of the third branch handle 2314 is fixed to the inside of the housing 2311, and the third branch handle 2314 is provided therein with a suture passing cavity running through the third branch handle 2314. The implant implantation mechanism further includes a locking suture delivery tube 234, wherein the locking suture delivery tube 234 passes through the bending-adjusting sheath tube 222, a proximal end of the locking suture delivery tube 234 is connected to a distal end of the third branch handle 2314, and the locking suture 104 passes through the locking suture delivery tube 234 and the suture passing cavity. Referring to FIG. 15, a compressing structure 600 is provided on the third branch handle 2314, and the compressing structure 600 is configured to tightly compress the locking suture 104 to the inside of the suture passing cavity.

Referring to FIG. 15, the third branch handle 2314 includes an end suture outlet bushing 23141 and a third connecting rod part 23142, wherein a distal end of the end suture outlet bushing 23141 is connected to the third connecting rod part 23142, the third connecting rod part 23142 is provided with a through-hole, a stepped hole is provided inside the end suture outlet bushing 23141, and a distal end of the stepped hole has a larger diameter than a proximal end of the stepped hole, in this way, a proximal end of the third connecting rod part 23142 is inserted inside the distal end of the end suture outlet bushing 23141.

In the present embodiment, the compressing structure 600 is an elastic pad, and the compressing structure 600 is squeezed between an end surface of the proximal end of the third connecting rod part 23142 and a step of the stepped hole. A wire passing hole is provided on the compressing structure 600. The proximal end of the locking suture 104, after passing through the third connecting rod part 23142 and the wire passing hole in sequence, extends out of the end suture outlet bushing 23141 from the proximal end of the stepped hole, and the compressing structure 600 tightly compresses the locking suture 104.

Figure 11:
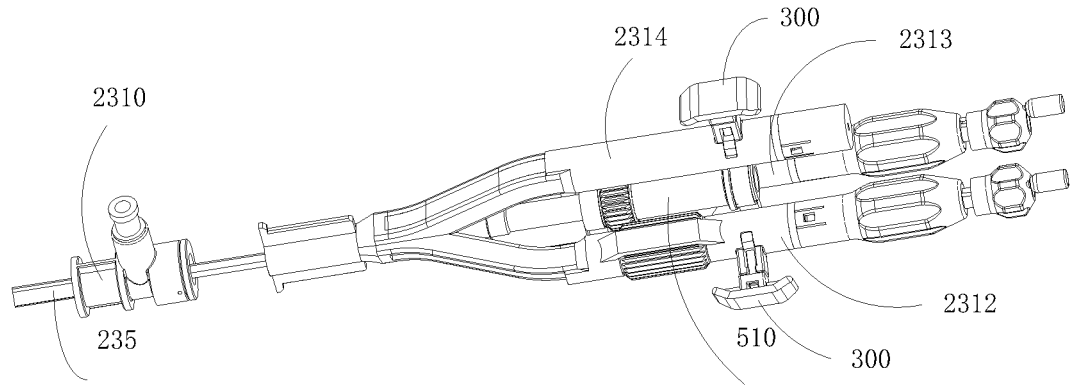
FIG. 11 is a schematic view of an overall structure of the implantation handle shown in FIG. 10 in a perspective in a housing-free state.

Besides, as shown in FIG. 11, FIG. 13, and FIG. 15, in other embodiments, the proximal end of the third connecting rod part 23142 can be engaged with a distal end of the end suture outlet bushing 23141, so as to prevent the third connecting rod part 23142 from rotating relative to the end suture outlet bushing 23141, thus reducing the possibility of loosening of the compressing structure 600. Alternatively, a unidirectional rotating structure 300 also may be provided at the distal end of the third connecting rod part 23142, and the anti-rotation effect is further enhanced with the unidirectional rotating structure 300. In addition, with reference to FIG. 11 to FIG. 13, in the present embodiment, the implant implantation mechanism further includes an equipartition tube 235, wherein the equipartition tube 235 passes through the bending-adjusting sheath tube 222, three delivery cavities are provided on the equipartition tube 235, and the first delivery tube 2321, the second delivery tube, and the locking suture delivery tube 234 pass through the three delivery cavities in one-to-one correspondence.

It can be understood that the first delivery tube 2321, the second delivery tube, and the locking suture delivery tube 234 pass through different delivery cavities respectively, and the equipartition tube 235 can separate the first delivery tube 2321, the second delivery tube, and the locking suture delivery tube 234, in this way, mutual interference between the first delivery tube 2321, the second delivery tube, and the locking suture delivery tube 234 can be avoided.

It is worth noting that, referring to FIG. 11 and FIG. 13, in the present embodiment, a sealing base 2310 is provided inside the implantation handle 231, the equipartition tube 235 passes through the sealing base 2310, and the sealing base 2310 can effectively block leakage of blood flowing out from the equipartition tube 235.

Figure 16:
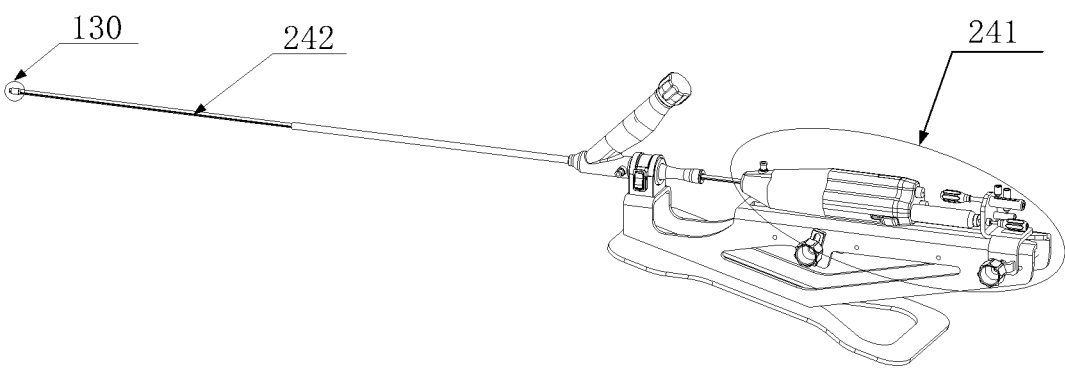
FIG. 16 is a schematic view of an overall structure of the repair assembly implantation device, mounted with a suture clamping device, provided in an embodiment of the present disclosure.
Figure 17:
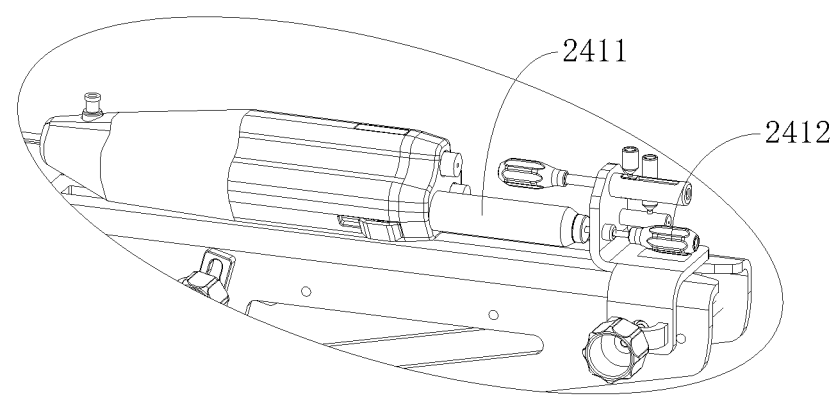
FIG. 17 is an enlarged view of a partial structure of the part of an operating handle of the repair assembly implantation device shown in FIG. 16.

In addition, referring to FIG. 16 and FIG. 17, in an optional example of the present embodiment, the implantation handle 231 is mounted on the support base 210 in a detachable manner. There are multiple specific detachable structures, for example, they are connected by screws or in other manners, and detached from each other by disassembling the screws, or the like. Alternatively, a sliding groove in communication with the external environment can be provided on a proximal end of the support base 210, and the implantation handle 231 is slidably mounted on the support base 210 through the sliding groove, etc.

In the present embodiment, the repair assembly implantation device further includes a suture-clamping-device implantation mechanism configured to implant the suture clamping device 130 into the human organs. The suture-clamping-device implantation mechanism includes an operating handle 241 and a suture-clamping-device delivery cable assembly 242, wherein the operating handle 241 is detachably mounted on the support base 210, a proximal end of the suture-clamping-device delivery cable assembly 242 is connected to the operating handle 241, a distal end of the suture-clamping-device delivery cable assembly 242 is configured to be capable of assembling or releasing the suture clamping device 130, the operating handle 241 is configured to deliver the suture clamping device 130 to the human organs and make the suture clamping device 130 tightly clamp the locking suture 104 of the first implant 110 and the locking suture 104 of the second implant 120.

In an optional embodiment, the repair assembly implantation device further includes a suture-clamping-device implantation mechanism; the suture-clamping-device implantation mechanism is configured to implant the suture clamping device 130 in the repair assembly provided in any optional example of Embodiment 1 into the human organs. As shown in FIG. 16 and FIG. 17, the suture-clamping-device implantation mechanism includes an operating handle 241 and a suture-clamping-device delivery cable assembly 242; the operating handle 241 is configured to be mounted to the support base 210 in a detachable manner in a working condition that the implantation handle 231 is not mounted to the support base 210; the suture-clamping-device delivery cable assembly 242 passes through the bending-adjusting sheath tube 222, a proximal end of the suture-clamping-device delivery cable assembly 242 is connected to the operating handle 241, a distal end of the suture-clamping-device delivery cable assembly 242 is configured to be capable of assembling or releasing the suture clamping device 130, the operating handle 241 is configured to be capable of delivering the suture clamping device 130 to the human organs and making the suture clamping device 130 tightly clamp the locking suture 104 of the first implant 110 and the locking suture 104 of the second implant 120. Specifically, in the present embodiment, as shown in FIG. 17, the operating handle 241 includes a rotating barrel 2411 and a knob 2412, the suture-clamping-device delivery cable assembly 242 includes a suture clamping device delivery tube, a distal end of the suture clamping device delivery tube is formed as a polygonal positioning portion, a polygonal through-hole capable of being snap-fitted with the polygonal positioning portion is provided on an end surface of a proximal end of the suture clamping device 130, and after the polygon positioning portion is snap-fitted with the polygon through-hole, the suture clamping device 130 and the suture clamping device delivery tube can rotate synchronously. The structure covered by the rotating barrel 2411 is the same as the structure of the foregoing first rotating portion 2021, and this structure is connected to the rotating barrel 2411 by means of splines or by means of concave-convex fitting structures, and the knob 2412 is connected to the rotating barrel 2411 fixedly or by means of splines or by means of concave-convex fitting structures.

The suture clamping device 130 is provided with two through holes, the two through holes can be configured to allow the two locking sutures 104 to pass therethrough, and a spring can be provided in each through hole so as to tightly clamp the locking suture 104. In this way, when the knob 2412 is rotated, the rotating barrel rotates therewith, and the rotating barrel drives the suture clamping device delivery tube to rotate, so as to slowly deliver the suture clamping device 130 into the human organs and tissues, the suture clamping device 130 tightly clamps the two locking sutures 104, and then exits the suture clamping device delivery tube.

In some embodiments:

As shown in FIG. 1 and FIG. 2, in FIG. 1 and FIG. 2, the repair assembly 100 includes a first implant 110, a second implant 120, and a suture clamping device 130. The first implant 110 and the second implant 120 each include a first fastener nail 101, a second fastener nail 102, a transverse tube 103, and a locking suture 104, an opposite end of a nail-in end of the first fastener nail 101 and an end of the transverse tube 103 are connected by a connecting wire 105, an opposite end of a nail-in end of the second fastener nail 102 and the other end of the transverse tube 103 are connected by a connecting wire 105, and the locking suture 104 is connected to the transverse tube 103, the suture clamping device 130 is configured to be capable of tightly clamping the locking suture 104 of the first implant 110 and the locking suture 104 of the second implant 120, so as to fix a spacing between the transverse tube 103 of the first implant 110 and the transverse tube 103 of the second implant 120. The first fastener nail 101 and the second fastener nail 102 each include a nail base 1011 and a helical portion 1012, an end of the helical portion 1012 is the nail-in end, an opposite end of the nail-in end of the helical portion 1012 is connected to the nail base 1011, and the nail base 1011 is connected to the connecting wire 105. The nail base 1011 is provided thereon with a wiring slot 106 configured to allow the connecting wire 105 to be embedded therein. The connecting wire 105 can be wound in the wiring slot 106. The outer tube walls of two ends of the transverse tube 103 are each provided with a wire winding slot 108 configured to allow the connecting wire 105 to be embedded therein. The connecting wire 105 can be wound in the wire winding slot 108.

As shown in FIG. 3 to FIG. 7, in FIG. 3 to FIG. 7, the bending-adjusting handles 221 of the two bending-adjusting sheath tube mechanisms can be respectively rotatably connected to the brackets of the two bending-adjusting sheath tube mechanisms through different rotating structures. The first delivery cable assembly 232 includes a first delivery tube 2321, a first delivery cable 2322, and a first pin 2323, a distal end of the first delivery tube 2321 is sleeved on the opposite end of the nail-in end of the first fastener nail 101, and the first delivery tube 2321 is configured to drive the first fastener nail 101 to rotate synchronously, the first delivery cable 2322 passes through the first delivery tube 2321, a proximal end of the first pin 2323 is fixedly connected to a distal end of the first delivery cable 2322, and a distal end of the first pin 2323 is in threaded connection to the opposite end of the nail-in end of the first fastener nail 101, so that the first fastener nail 101 and the first delivery tube 2321 rotate synchronously. The proximal end of the first pin 2323 abuts against the distal end of the first delivery cable 2322 through a tapered surface 230, the diameter of the tapered surface 230 gradually increases in a direction from the first pin 2323 to the first delivery cable 2322. The implant implantation mechanism further includes a locking suture delivery tube 234, a proximal end of the locking suture delivery tube 234 is connected to a distal end of the third branch handle 2314, and the locking suture 104 can pass through the locking suture delivery tube 234.

As shown in FIG. 8, in FIG. 8, the bending-adjusting handle 221 includes a bending-adjusting knob 2210, a bending-adjusting screw rod 2211, and an adjusting block 2212, the adjusting block 2212 is sleeved over the bending-adjusting screw rod 2211 in a threaded manner, a bending-adjusting wire is connected between a proximal end of the bending-adjusting sheath tube 222 and the adjusting block 2212, and a proximal end of the bending-adjusting screw rod 2211 is connected to the bending-adjusting knob 2210.

As shown in FIG. 9, in FIG. 9, the rotating structure includes an upper rotating shell 2241, a lower rotating shell 2242, and a rotating buckle 2243, wherein the lower rotating shell 2242 is fixed to the support base 210, and the upper rotating shell 2241 and the lower rotating shell 2242 are connected by the rotating buckle 2243. The translation assembly 223 includes an adjusting rack 2233, a limiting block 2234, an adjusting knob 2231, and an adjusting gear 2232, wherein the adjusting rack 2233 is mounted on a bracket of the bending-adjusting sheath tube mechanism at the proximal end, the limiting block 2234 is connected to the support base 210, the limiting block 2234 is provided with a limiting long hole, one end of the adjusting knob 2231 is fixedly connected to a rotating shaft slidably cooperating with the foregoing limiting long hole, the adjusting gear 2232 is fixedly connected to an end of the rotating shaft away from the adjusting knob 2231, and the adjusting gear 2232 can be meshed with the adjusting rack 2233.

Figure 10:
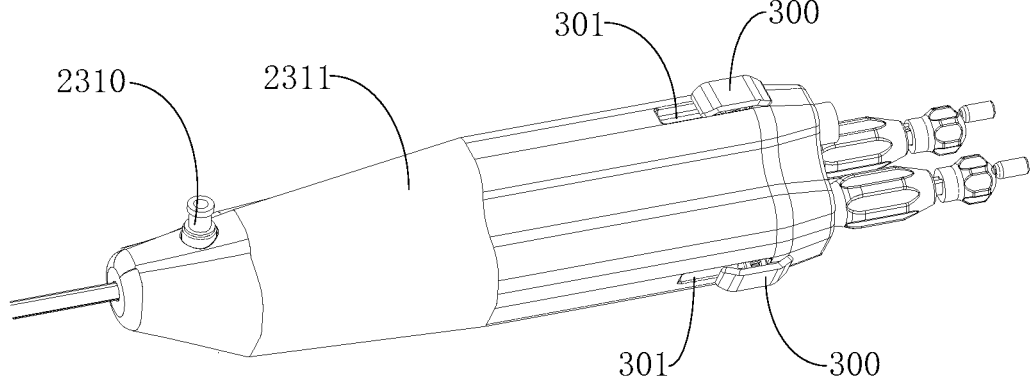
FIG. 10 is a schematic view of an overall structure of an implantation handle in an implant implantation mechanism of the repair assembly implantation device provided in an embodiment of the present disclosure.

As shown in FIG. 10, in FIG. 10, the unidirectional rotating structure 300 is located between the first rotating portion 2021 and the main tube 201, and the unidirectional rotating structure 300 is configured to enable the first rotating portion 2021 to unidirectionally rotate only with respect to the main tube 201. The housing 2311 of the implantation handle 231 is provided thereon with an avoidance hole 301 for the pawl member 320 to extend out. A sealing base 2310 is provided inside the implantation handle 231, and the sealing base 2310 can prevent blood leakage.

Figure 12:
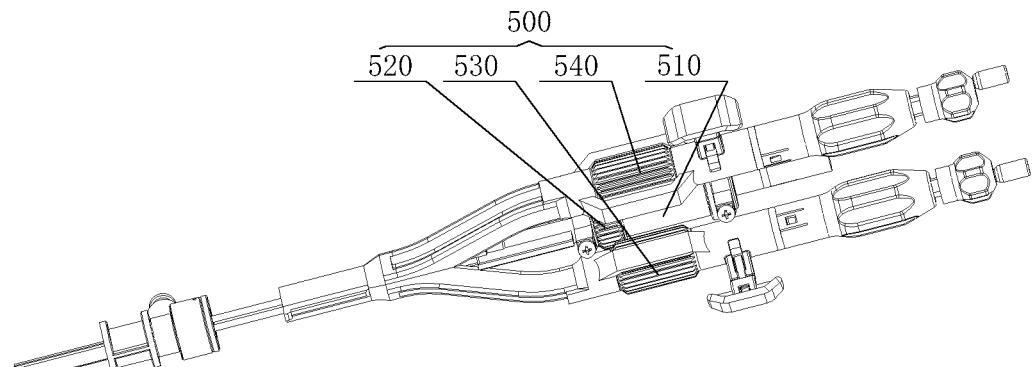
FIG. 12 is a schematic view of an overall structure of the implantation handle shown in FIG. 10 in another perspective in the housing-free state.

As shown in FIG. 11 to FIG. 13, in FIG. 11 to FIG. 13, the implantation handle 231 further includes a third branch handle 2314, and a distal end of the third branch handle 2314 is connected to an inner wall of the housing 2311. The rotating portion 202 includes a first rotating portion 2021 and a second rotating portion 2022, a distal end of the first rotating portion 2021 is rotatably sleeved on the proximal end of the main tube 201, a distal end of the second rotating portion 2022 is rotatably sleeved on the first rotating portion 2021, and the second rotating portion 2022 and a proximal end of the first rotating portion 2021 are both located outside the housing 2311. The implantation handle 231 further includes a push structure 500, wherein the push structure 500 includes a push handle 510, a first gear 520, a second gear 530, and a third gear 540, the push handle 510 is connected to the main frame, the first gear 520, the second gear 530, and the third gear 540 are meshed in turn, moreover, the first gear 520 is connected to the first rotating portion 2021 of the first branch handle 2312, the second gear 530 is connected to the push handle 510, and the third gear 540 is connected to the first rotating portion 2021 of the second branch handle 2313. A limiting hole 2011 is provided on a tube wall of the main tube 201. The unidirectional rotating structure 300 is located between the first rotating portion 2021 and the main tube 201, and the unidirectional rotating structure 300 is configured to enable the first rotating portion 2021 to unidirectionally rotate only with respect to the main tube 201.

As shown in FIG. 14, in FIG. 14, the second rotating portion 2022 includes a second connecting rod part 2005 and a second rotating shell 2006, the second connecting rod part 2005 is inserted inside the first rotating shell 2003, the second rotating shell 2006 is connected to a proximal end of the second connecting rod part 2005, and a proximal end of the helical spring 2004 is connected to a distal end of the second connecting rod part 2005. The first gear 520 is connected to the outside of the end connector 2001 of the first rotating portion 2021 of the first branch handle 2312. The first rotating portion 2021 includes an end connector 2001, a first connecting rod part 2002, and a first rotating shell 2003 which are connected in sequence, the end connector 2001 and the first connecting rod part 2002 are inserted inside the main tube 201, the unidirectional rotating structure 300 includes a pawl member 320 and a ratchet 310 provided on an outer circumferential surface of the first connecting rod part 2002, and the pawl of the pawl member 320 and the ratchet 310 are meshed with each other.

As shown in FIG. 15, in FIG. 15, a compressing structure 600 is provided on the third branch handle 2314, and the compressing structure 600 is configured to tightly compress the locking suture 104 to the inside of the suture passing cavity.

As shown in FIG. 16 and FIG. 17, in FIG. 16 and FIG. 17, the operating handle 241 includes a rotating barrel 2411 and a knob 2412, and the knob 2412 and the rotating barrel 2411 are fixedly connected or connected by means of splines or connected by means of concave-convex fitting structures.

The effects that can be achieved by other same structures in the present embodiment as those in Embodiment 1 can be obtained with reference to various optional or preferred examples of Embodiment 1. Finally, it should be explained that the various embodiments above are merely used for illustrating the technical solutions of the present disclosure, rather than limiting the present disclosure; although the detailed descriptions are made to the present disclosure with reference to various preceding embodiments, those ordinarily skilled in the art should understand that they still could modify the technical solutions described in various preceding examples, or make equivalent substitutions to some or all of the technical features therein; and these modifications or substitutions do not make the corresponding technical solutions essentially depart from the scope of the technical solutions of various embodiments of the present disclosure.

INDUSTRIAL APPLICABILITY

To sum up, the present disclosure provides a repair assembly and a repair assembly implantation device, which can shorten the operation time, and is conducive to rapid recovery of patients after the surgery.

What is claimed is:
1. A repair assembly implantation device, comprising an implant implantation mechanism and the repair assembly, the implant implantation mechanism being configured to implant the repair assembly into a human organ, wherein the repair assembly comprises a first implant, a second implant, and a suture clamping device, wherein the first implant and the second implant each comprise a first fastener nail, a second fastener nail, a transverse tube, and a locking suture; an opposite end of a nail-in end of the first fastener nail is connected with an end of the transverse tube by a connecting wire, and an opposite end of a nail-in end of the second fastener nail is connected with the other end of the transverse tube by a connecting wire, and the locking suture is connected to the transverse tube;

the suture clamping device is configured to be capable of tightly clamping the locking suture of the first implant and the locking suture of the second implant, so as to fix a spacing between the transverse tube of the first implant and the transverse tube of the second implant;

wherein the repair assembly implantation device comprises a support base, the implant implantation mechanism comprises an implantation handle, a first delivery cable assembly, and a second delivery cable assembly, wherein the implantation handle is mounted on the support base, and a proximal end of the first delivery cable assembly and a proximal end of the second delivery cable assembly are both connected to the implantation handle, wherein the first delivery cable assembly is configured to implant the first fastener nail under a driving effect of the implantation handle; and the second delivery cable assembly is configured to implant the second fastener nail under the driving effect of the implantation handle;

wherein the implantation handle comprises a housing, a first branch handle, and a second branch handle, the housing is mounted to the support base, the first branch handle and the second branch handle each comprise a main tube and a rotating portion, the main tube is inserted inside the housing, a distal end of the rotating portion is rotatably inserted inside a proximal end of the main tube, and a proximal end of the rotating portion is located outside the housing;

the distal end of the rotating portion of the first branch handle is connected to the proximal end of the first delivery cable assembly, and the distal end of the rotating portion in the second branch handle is connected to the proximal end of the second delivery cable assembly;

wherein the first delivery cable assembly comprises a first delivery tube, a first delivery cable, and a first pin, a distal end of the first delivery tube is sleeved on the opposite end of the nail-in end of the first fastener nail, the first delivery tube is configured to drive the first fastener nail to rotate synchronously, the first delivery cable passes through the first delivery tube, a proximal end of the first pin is fixedly connected to a distal end of the first delivery cable, and a distal end of the first pin can be in threaded connection with the opposite end of the nail-in end of the first fastener nail, so that the first fastener nail and the first delivery tube rotate synchronously; and/or the second delivery cable assembly comprises a second delivery tube, a second delivery cable, and a second pin, a distal end of the second delivery tube is sleeved on the opposite end of the nail-in end of the second fastener nail, the second delivery tube is configured to drive the second fastener nail to rotate synchronously, the second delivery cable passes through the second delivery tube, a distal end of the second pin can be in threaded connection with a distal end of the second delivery cable, and the distal end of the second pin can be in threaded connection with the opposite end of the nail-in end of the second fastener nail, so that the second fastener nail and the second delivery tube rotate synchronously;

wherein the rotating portion comprises a first rotating portion and a second rotating portion, a distal end of the first rotating portion is rotatably sleeved on the proximal end of the main tube, a distal end of the second rotating portion is rotatably sleeved on the first rotating portion, and the second rotating portion and a proximal end of the first rotating portion are both located outside the housing;

wherein in the first branch handle, the distal end of the first rotating portion is connected to a proximal end of the first delivery tube, and the distal end of the second rotating portion is connected to the proximal end of the first delivery cable; and in the second branch handle, the distal end of the first rotating portion is connected to a proximal end of the second delivery tube, and the distal end of the second rotating portion is connected to the proximal end of the second delivery cable.

2. The repair assembly implantation device according to claim 1, wherein the first branch handle and the second branch handle each comprise a helical spring;

in the first branch handle, the distal end of the second rotating portion is connected to the proximal end of the first delivery cable by the helical spring; and in the second branch handle, the distal end of the second rotating portion is connected to the proximal end of the second delivery cable by the helical spring.

3. The repair assembly implantation device according to claim 1, wherein the first branch handle and the second branch handle each further comprise a unidirectional rotating structure, and wherein in the first branch handle and/or the second branch handle: the unidirectional rotating structure is located between the first rotating portion and the main tube, and the unidirectional rotating structure is configured to enable the first rotating portion to unidirectionally rotate only with respect to the main tube.

4. The repair assembly implantation device according to claim 1, wherein the first branch handle and the second branch handle each further comprise an anti-rotation protection element, and in the first branch handle and/or the second branch handle: the anti-rotation protection element is detachably connected to the first rotating portion and the second rotating portion simultaneously, and the anti-rotation protection element is configured to make the first rotating portion and the second rotating portion synchronously rotate.

5. The repair assembly implantation device according to claim 1, wherein the main tube of the first branch handle and the main tube of the second branch handle are connected to each other to form a main frame, and the main frame is slidably inserted inside the housing.

6. The repair assembly implantation device according to claim 5, wherein the implantation handle further comprises a push structure, the push structure comprises a push handle, a first gear, a second gear, and a third gear, the push handle is connected to the main frame, the first gear, the second gear, and the third gear are meshed in turn, moreover, the first gear is connected to the first rotating portion of the first branch handle, the second gear is connected to the push handle, and the third gear is connected to the first rotating portion of the second branch handle.

7. The repair assembly implantation device according to claim 1, wherein the implantation handle further comprises a third branch handle, a distal end of the third branch handle is connected to an inner wall of the housing, and the third branch handle is provided with a suture passing cavity running therethrough;

the implant implantation mechanism further comprises a locking suture delivery tube, wherein a proximal end of the locking suture delivery tube is connected to the distal end of the third branch handle, and the locking suture passes through the locking suture delivery tube and the suture passing cavity simultaneously.

8. The repair assembly implantation device according to claim 7, wherein a compressing structure is provided on the third branch handle, and the compressing structure is configured to compress the locking suture to an inside of the suture passing cavity.

9. The repair assembly implantation device according to claim 7, wherein the implant implantation mechanism further comprises an equipartition tube, wherein three delivery cavities are provided on the equipartition tube, and the first delivery tube, the second delivery tube, and the locking suture delivery tube pass through the three delivery cavities in one-to-one correspondence.

10. The repair assembly implantation device according to claim 1, wherein the repair assembly implantation device further comprises a suture-clamping-device implantation mechanism configured to implant the suture clamping device into a human organ, the suture-clamping-device implantation mechanism comprises an operating handle and a suture-clamping-device delivery cable assembly, the operating handle is detachably mounted on the support base, a proximal end of the suture-clamping-device delivery cable assembly is connected to the operating handle, a distal end of the suture-clamping-device delivery cable assembly is configured to be capable of assembling or releasing the suture clamping device, the operating handle is configured to deliver the suture clamping device to the human organ and make the suture clamping device tightly clamp the locking suture of the first implant and the locking suture of the second implant.

11. The repair assembly implantation device according to claim 1, wherein the repair assembly implantation device further comprises at least one bending-adjusting sheath tube mechanism, the at least one bending-adjusting sheath tube mechanism comprises a bending-adjusting handle and a bending-adjusting sheath tube, the bending-adjusting handle is mounted on the support base, the bending-adjusting sheath tube is connected to the bending-adjusting handle, and the first delivery cable assembly and the second delivery cable assembly both pass through the bending-adjusting sheath tube.

12. The repair assembly implantation device according to claim 1, wherein the first fastener nail and the second fastener nail each comprise a nail base and a helical portion, an end of the helical portion is the nail-in end, an opposite end of the nail-in end of the helical portion is connected to the nail base, and the nail base is connected to the connecting wire.

13. The repair assembly implantation device according to claim 12, wherein the nail base is provided thereon with a wiring slot configured to allow the connecting wire to be embedded therein.

14. The repair assembly implantation device according to claim 1, wherein an outer tube wall of the transverse tube is provided with a suture locking slot configured to allow the locking suture to be embedded therein.

15. The repair assembly implantation device according to claim 1, wherein outer tube walls of two ends of the transverse tube are each provided with a wire winding slot configured to allow the connecting wire to be embedded therein; or alternatively, the two ends of the transverse tube are each provided with a wire passing hole, and the connecting wire is configured to pass through the wire passing hole, so as to be fixedly connected to the transverse tube.

* * * * *